United States Patent
Zagorchev et al.

(10) Patent No.: US 10,426,430 B2
(45) Date of Patent: Oct. 1, 2019

(54) AUTOMATED THREE DIMENSIONAL AORTIC ROOT MEASUREMENT AND MODELING

(75) Inventors: Lyubomir Georgiev Zagorchev, Burlington, MA (US); Michael Cardinale, Nottingham, NH (US); Scott Holland Settlemier, Marlborough, MA (US); Kevin CamHong Quan, Nashua, NH (US); Sabine Mollus, Aachen (DE); Juergen Weese, Aachen (DE); Ivan Salgo, Pelham, MA (US)

(73) Assignee: Koninklijke Philips N.V., Eindhoven (NL)

( * ) Notice: Subject to any disclaimer, the term of this patent is extended or adjusted under 35 U.S.C. 154(b) by 728 days.

(21) Appl. No.: 13/818,042

(22) PCT Filed: Aug. 24, 2011

(86) PCT No.: PCT/IB2011/053710
§ 371 (c)(1),
(2), (4) Date: May 6, 2013

(87) PCT Pub. No.: WO2012/025889
PCT Pub. Date: Mar. 1, 2012

(65) Prior Publication Data
US 2013/0231564 A1 Sep. 5, 2013

Related U.S. Application Data

(60) Provisional application No. 61/377,228, filed on Aug. 26, 2010.

(51) Int. Cl.
*A61B 8/00* (2006.01)
*A61B 8/08* (2006.01)
(Continued)

(52) U.S. Cl.
CPC .......... *A61B 8/0891* (2013.01); *A61B 8/0883* (2013.01); *A61B 8/145* (2013.01);
(Continued)

(58) Field of Classification Search
USPC .................................................. 600/437, 443
See application file for complete search history.

(56) References Cited

U.S. PATENT DOCUMENTS

| 5,997,479 A | 12/1999 | Savord |
| 6,013,032 A | 1/2000 | Savord |

(Continued)

FOREIGN PATENT DOCUMENTS

| WO | 9955233 A1 | 11/1999 |
| WO | 0007501 A1 | 2/2000 |
| WO | 2010150156 A1 | 12/2010 |

OTHER PUBLICATIONS

Sermesant et al. "Deformable Biomechanical Models: Application to 4D Cardiac Image Analysis" Medical Image Analysis, Oxford University Press, Oxford, GB, vol. 7, No. 4, Dec. 1, 2003; pp. 4750-488.

(Continued)

*Primary Examiner* — Jonathan Cwern

(57) ABSTRACT

An ultrasound system for planning a surgical implantation of a prosthetic aortic valve produces three dimensional images of the aortic root region of a patient. An electronic model of an aortic root is accessed and fitted to the aortic root in a three dimensional ultrasound image. Preferably the aortic root model exhibits closed contour cross-sections which are fitted to the endothelial lining of the aortic root in the ultrasound image. A medial axis of the fitted model is identified and radii measured from the medical axis to the border of the fitted model. The radii are joined to identify a surface forming a mesh model fitted to the aortic root anatomy of the patient. The shape and dimensions of the (Continued)

fitted model may be used to fabricate a custom prosthetic valve for aortic valve replacement.

15 Claims, 9 Drawing Sheets

(51) Int. Cl.
    *A61B 8/14*       (2006.01)
    *G06T 7/12*       (2017.01)
    *G06T 7/149*     (2017.01)
    *G06T 7/62*       (2017.01)
    *G06T 7/66*       (2017.01)
    *A61B 5/107*     (2006.01)
    *A61B 34/10*     (2016.01)

(52) U.S. Cl.
    CPC .............. *A61B 8/466* (2013.01); *A61B 8/483* (2013.01); *A61B 8/5207* (2013.01); *A61B 8/5223* (2013.01); *G06T 7/12* (2017.01); *G06T 7/149* (2017.01); *G06T 7/62* (2017.01); *G06T 7/66* (2017.01); *A61B 5/1075* (2013.01); *A61B 8/543* (2013.01); *A61B 34/10* (2016.02); *A61B 2034/105* (2016.02); *G06T 2207/10136* (2013.01); *G06T 2207/30101* (2013.01); *G06T 2207/30172* (2013.01)

(56) References Cited

U.S. PATENT DOCUMENTS

| | | | |
|---|---|---|---|
| 6,106,466 A * | 8/2000 | Sheehan et al. ............. 600/443 | |
| 6,572,547 B2 | 6/2003 | Miller | |
| 7,010,164 B2 | 3/2006 | Weese et al. | |
| 2004/0101184 A1 * | 5/2004 | Sivaramakrishna et al. ................ | 382/131 |
| 2004/0249270 A1 * | 12/2004 | Kondo .................... G06T 15/08 | 600/425 |
| 2005/0281447 A1 * | 12/2005 | Moreau-Gobard ....... G06T 7/12 | 382/130 |
| 2006/0182341 A1 | 8/2006 | Rinck et al. | |
| 2008/0201007 A1 * | 8/2008 | Boyden .................... A61F 2/06 | 700/119 |
| 2009/0292349 A1 * | 11/2009 | Golesworthy ............... 623/1.15 | |
| 2010/0032145 A1 | 2/2010 | Lee | |
| 2010/0070249 A1 | 3/2010 | Ionasec et al. | |
| 2010/0131039 A1 * | 5/2010 | Chau ..................... A61F 2/2418 | 623/1.12 |
| 2010/0157041 A1 * | 6/2010 | Klaiman et al. ................ 348/77 | |
| 2010/0166283 A1 | 7/2010 | Grosskopf | |
| 2010/0240996 A1 * | 9/2010 | Ionasec ................. G06T 7/0016 | 600/443 |
| 2012/0053466 A1 | 3/2012 | Bianchi et al. | |

OTHER PUBLICATIONS

Ecabert et al. "Automatic Model-Based Segmentation of the Heart in CT Images" IEEE Transactions on Medical Iamging, vol. 27, No. 9, Sep. 2008, pp. 1189-1201.

Gautier M, et al "Nomograms for aortic root diameters in children using two-dimensional echocardiography" Am J Cardiol. Mar. 15, 2010;105(6):888-94.

J. Weese et al, Shape constrained deformable models for 3D medical image segmentation. In M. F. Insana and R. M. Leahy, editors, Image Processing in Medical Imaging (IPMI), vol. 2082 of LNCS, pp. 380-387. Springer, Jun. 2001.

* cited by examiner

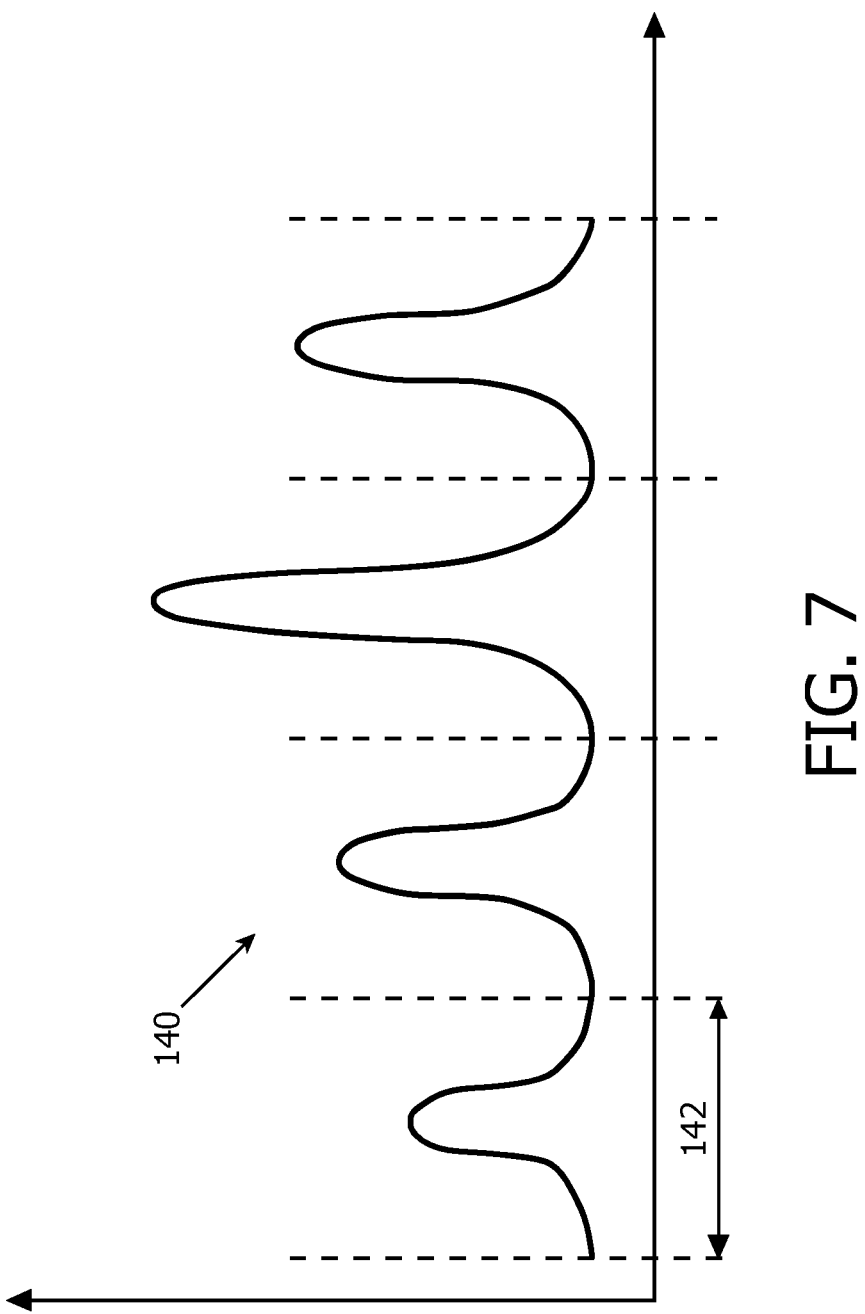

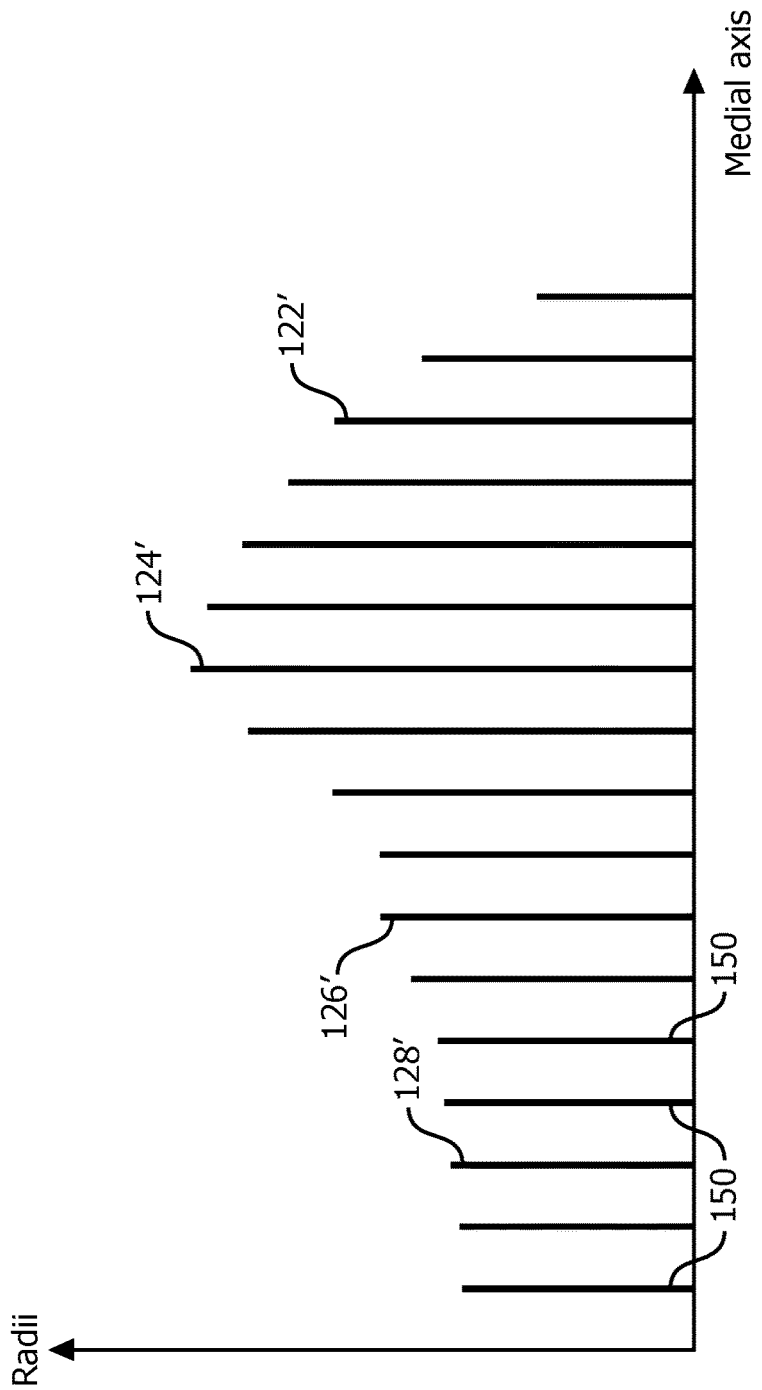

AUTOMATED THREE DIMENSIONAL AORTIC ROOT MEASUREMENT AND MODELING

This invention relates to medical diagnostic ultrasound systems and, in particular, to ultrasound systems which perform three dimensional modeling and measurement of the aortic root using three dimensional ultrasound images.

International patent application no. U.S.2010/32145 (Bianchi et al.), filed Apr. 23, 2010 describes an automated ultrasonic imaging method for performing virtual sizing of anatomy for the implantation of prosthetic cardiovascular devices such as heart valves. The method is performed by calling up a scaled electronic image of a sizer for a prosthetic device, which is an image of a physical sizer used to assess the size of the device needed for an anatomical implant site of a particular size. The user manipulates this "virtual sizer" in a correspondingly scaled three dimensional ultrasound image of the anatomical site for the implant. By trying virtual sizers of different sizes in the 3D image of the anatomy the user can determine the appropriate device size to be used in the implant procedure.

The use of the virtual sizer works well for devices which are produced in a range of pre-set sizes and which come with sizers to select the appropriately sized device. However some implantable devices are custom-built to a patient's measured anatomy. For such custom devices it is necessary to measure the anatomical site of the implant first, then provide this data to the device manufacturer, whereupon the manufacturer can produce an implant device to the exact dimensions required for the patient. After the device is manufactured it is supplied to the surgeon for the implant procedure, which guarantees that the supplied device is of the size required by the patient. It is desirable of course to be able to measure the implant site by a minimally invasive technique, and most preferably by a completely noninvasive technique, so that the patient only has to undergo one surgical procedure, the one in which the finished device is implanted.

In accordance with the principles of the present invention, an ultrasound system includes electronic image data which models different aspects of the cardiovascular system. The data may be in the form of a heart model library, which models the size and shape of the heart and its related anatomy. In an implementation of the present invention the library contains a model of the aortic root, which is selected by the user. The ultrasound system produces a three dimensional image of the outflow tract of the heart, including the aortic root and its jointure to the ascending aorta. The aortic root model includes shapes of the internal dimensions of the aortic root which, in a constructed embodiment, are closed contour cross-sections at key anatomical locations in the aortic root. A 3D shape processor then adjusts parameters of the starting aortic root model to fit the closed contour shapes of the model, such as circles and ellipses, to the internal anatomy of the aortic root in the 3D ultrasound image. The resultant scaled model is thus sized and shaped to the dimensions and characteristics of the patient's aortic root. The scaled model and its dimensions may then be provided to a manufacturer of an aortic valve prosthesis, who may then construct a replacement valve of the exact size and shape required for the patient.

In the drawings:

FIG. 7 illustrates a histogram of size measurements of different cross-sections of an adjusted aortic root model.

FIG. 8 illustrates a spatial sequence of cross-sectional size measurements used to form a finally adjusted 3D model of the internal dimensions of an aortic root.

Figure 1:
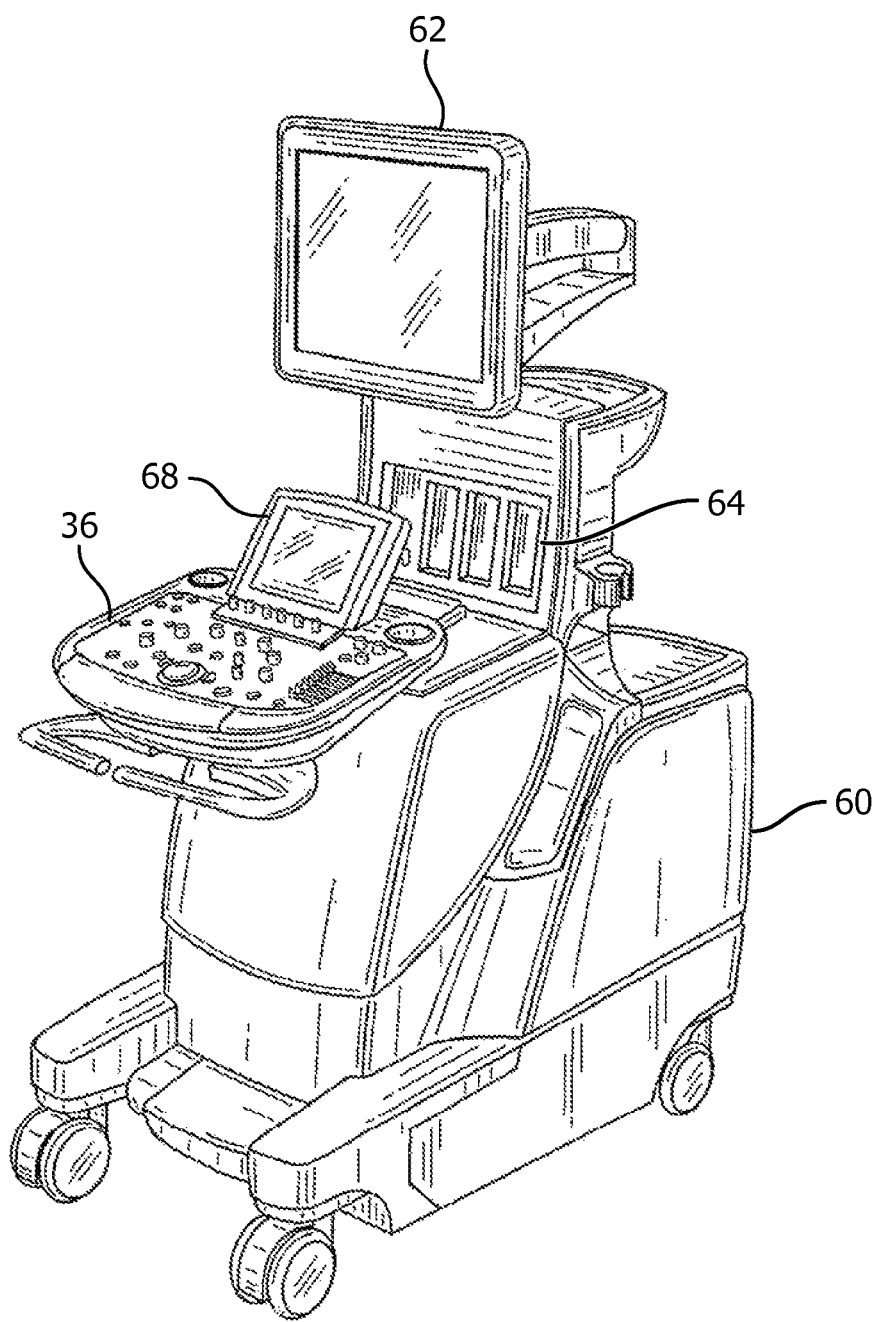
FIG. 1 is an illustration of a cart-borne ultrasound system for three-dimensional imaging.

Referring first to FIG. 1, an ultrasound system constructed in accordance with the principles of the present invention is shown. The ultrasound system includes a main frame or chassis 60 containing most of the electronic circuitry for the system. The chassis 60 is wheel-mounted for portability. An image display 62 is mounted on the chassis 60. Different imaging probes may be plugged into three connectors 64 on the chassis. In an implementation of the present invention a matrix array probe which performs 3D imaging with a two-dimensional array transducer is plugged into a connector 64 and used to acquire three dimensional (3D) ultrasound images of the aortic root of a patient. A semi-invasive probe such as a matrix TEE probe may also be used. The advantage of the matrix TEE probe is that the heart and aortic root can be imaged through tissue from the esophagus immediately behind the heart without the interference from the ribs that is encountered by a trans-thoracic probe imaging from the thorax. A matrix TEE probe is described in U.S. Pat. No. 6,572,547 (Miller et al.) The chassis 60 includes a control panel with a keyboard and controls, generally indicated by reference numeral 36, by which a sonographer operates the ultrasound system and enters information about the patient or the type of examination that is being conducted. At the back of the control panel 36 is a touchscreen display 68 on which programmable softkeys are displayed for specific control functions. The sonographer selects a softkey on the touchscreen display 68 simply by touching the image of the softkey on the display. At the bottom of the touchscreen display is a row of buttons, the functionality of which varies in accordance with the softkey labels on the touchscreen immediately above each button.

Figure 2:
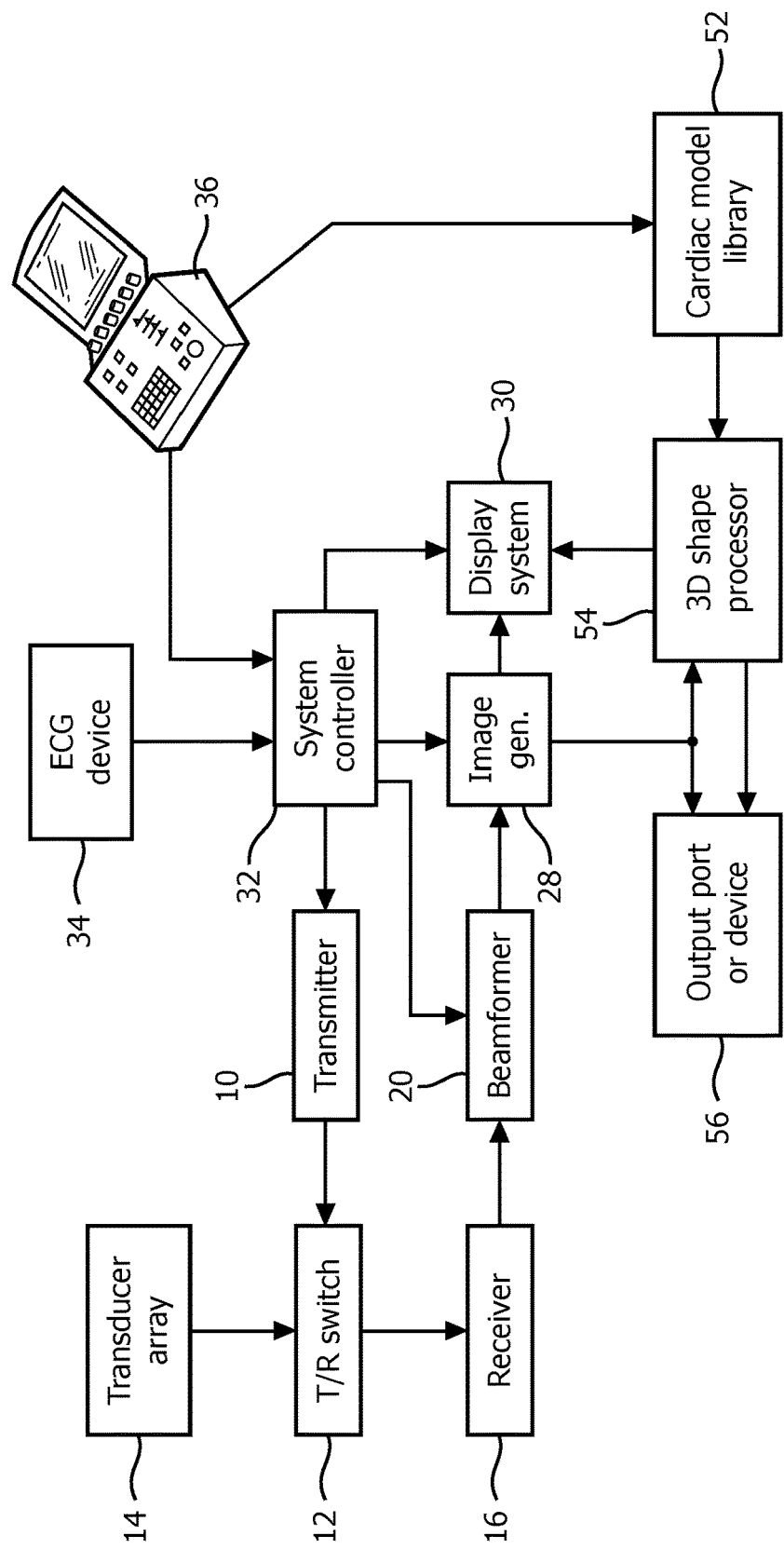
FIG. 2 is a block diagram of the 3D ultrasound system of FIG. 1 constructed in accordance with the principles of the present invention.

A block diagram of the major elements of an ultrasound system of the present invention is shown in FIG. 2. An ultrasound transmitter 10 is coupled through a transmit/receive (T/R) switch 12 to the transducer array 14 of the probe. Transducer array 14 is a two-dimensional array (matrix array) of transducer elements for performing three-dimensional scanning. The transducer array 14 transmits ultrasound energy into a volumetric region being imaged and receives reflected ultrasound energy, or echoes, from various structures and organs within the region. The transmitter 10 includes a transmit beamformer which controls the delay timing by Which the signals applied to elements of the transducer array are timed to transmit beams of a desired steering direction and focus. By appropriately delaying the pulses applied to each transducer element by transmitter 10, the transmitter 10 transmits a focused ultrasound beam along a desired transmit scan line path through a volumetric region of the body such as the chest and heart. The transducer array 14 is coupled through T/R switch 12 to an ultrasound receiver 16. Reflected ultrasound energy from points within the volumetric region is received by the transducer elements at different times. The transducer elements convert the received ultrasound energy to received electrical signals which are amplified by receiver 16 and supplied to a receive beamformer 20. The signals from each transducer element are individually delayed and then are summed by the beamformer 20 to provide a beamformed signal that is a representation of the reflected ultrasound energy level along points on a given receive scan line. As known in the art, the delays applied to the received signals may be varied during reception of ultrasound energy to effect receive beam steering and dynamic focusing. The process is repeated for multiple scan lines directed throughout the volumetric region to provide signals for generating one or more two and three dimensional images of the volumetric region as described below. Because the transducer array is two-dimensional, the receive scan lines can be steered in azimuth and in elevation to form a three-dimensional scan pattern. The beamformed signals may undergo signal processing such as filtering, Doppler processing, and image processing and buffering by an image generator 28 which produces images of different volume segments or subvolumes of a maximum volumetric region. The image data is output from image generator 28 to a display system 30 which produces a three-dimensional image of the region of interest from the image data for display on the image display 62. The display system may also construct one or more 2D image planes of the region from the three dimensional image data, a process known as multiplanar reconstruction (MPR). The image generator 28 includes a scan converter which converts sector scan signals from beamformer 20 to conventional raster scan display signals. The image generator 28 also includes a volume renderer to produce three dimensional images of the imaged anatomy in the volumetric region. A system controller 32 provides overall control of the system in response to user inputs from the user controls of the control panel 36 and internally stored data. The system controller 32 performs timing and control functions and typically includes a microprocessor and associated memory. The system controller is responsive to signals received from the control panel 36 and touchscreen display 68 through manual or voice control by the system user.

An ECG device 34 includes ECG electrodes attached to the patient. The ECG device 34 supplies ECG waveforms to system controller 32 for display during a cardiac exam. The ECG signals may also be used during certain exams to synchronize imaging to the patient's cardiac cycle. For example, the ECG signal may be used to acquire an image of the aortic root at end systole when contraction of the heart is at the peak of forcing blood into the aorta and the aortic root is at its maximally expanded size and shape.

In a constructed embodiment portions of the transmit and received circuitry is located in the probe with the two dimensional transducer array in an integrated circuit assembly known as a micro beamformer. The micro beamformer performs at least partial beamforming of transmit and receive signals inside the probe, which reduces the number of signal lines in the probe cable which connects the probe to the system chassis 60. In a typical implementation the remainder of the receive beamforming is performed in the beamformer of the system mainframe, as is subsequent image processing and display. Micro beamformers for 3D imaging are described in U.S. Pat. No. 5,997,479 (Savord et al.) and U.S. Pat. No. 6,013,032 (Savord).

The ultrasound system of FIG. 2 includes a cardiac model library 52 and an automated 3D shape processor 54. A heart model stored in the library 52 may contain shapes and/or meshes of selected regions of the heart and cardiovascular system, such as the atria, ventricles, epicardial boundary and endocardial border shapes of the chambers of the heart. See U.S. Pat. No. 7,010,164 (Weese et al.) and "Automatic Model-Based Segmentation of the Heart in CT Images" by Ecabert et al., published in *IEEE Trans. On Med. Imaging*, vol. 27, no. 9 (September 2008) at pp 1189-1201. In accordance with the present invention the cardiac model library 52 includes a model of the aortic root as described below. The aortic root model is selected and coupled to the 3D shape processor 54, which also received a 3D ultrasound image of an aortic root from the image generator 28. The 3D shape processor then adjusts parameters of the aortic root model to fit the anatomy of the aortic root as shown in the 3D ultrasound image. The output from the 3D shape processor, which may be one or more measurements of the patient's aortic root, a scaled model of the patient's aortic root, or both, is then shown on the display system 30. The cardiac model library 52 and an automated 3D shape processor 54 may be included in the cart-borne ultrasound system for on-board analysis or may be located in a separate workstation which receives the 3D ultrasound image and performs the measurement, analysis, and display of the results in a remote analysis setting.

Figure 3A:
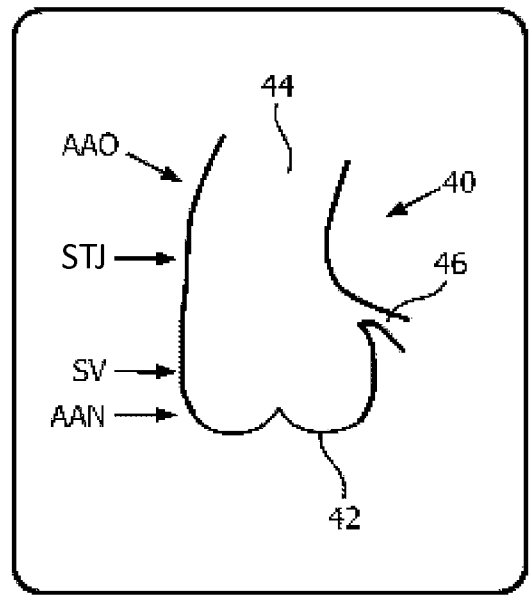
FIG. 3a illustrates a two dimensional ultrasound image of the aortic root.

FIG. 3a illustrates a two dimensional image of the aortic root, including the aortic valve 42 and a connecting portion of the ascending aorta. Acquiring a 2D image of the aortic root suitable for quantification and measurement can be difficult. One set of significant measurements to be done on the aortic root is the diameters of key landmarks of the aortic root. Four such landmark locations are indicated with the 2D image of FIG. 3a, including the aortic annulus (AAN) where the aortic valve is attached, the sinuses of valsalva (SV) which is the large diameter region following the aortic valve, the sinotubular junction (STJ) where the orifice narrows to the general diameter of the aorta, and the ascending aorta (AAO) thereafter. Another set of landmarks which is important for prosthetic valve design are the locations of the coronary artery ostia, one of which is shown at 46. In order to accurately measure the diameter across the aortic root at these landmark locations it is necessary for the 2D image plane to precisely and continuously pass through the medial (central) axis of the aortic root. Such a 2D image may be impossible to acquire as the medial axis may not be located in a single plane but can curve with undulations of the aortic root anatomy. Furthermore, even if an accurate measure of these diameters can be obtained, they may be accurate at only a single diameter through the lumen being measured, as it cannot be assumed that any of these anatomical locations are circular. Measurements of a 2D image of the aortic root for valve replacement can lead to the implantation of an incorrectly sized valve which can fit poorly, leak, or both.

Figure 3B:
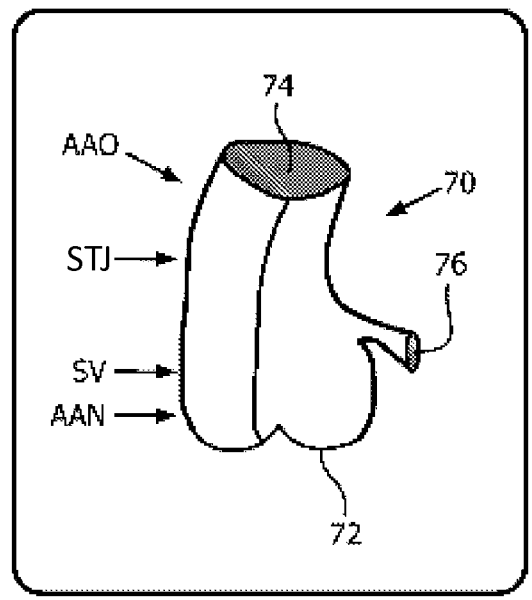
FIG. 3b illustrates a three dimensional ultrasound image of the aortic root.

In accordance with one aspect of the present invention, a 3D ultrasound image is used to measure the aortic root as illustrated by 3D image 70 in FIG. 3b. The 3D image 70 display not simply a "slice plane" through the aortic root, but a full image of the shape of the aortic root, the aortic valve 72, the aorta 74 and the coronary ostia 76. The same landmarks of the aortic valve shown in FIG. 3a are also indicated with respect to the 3D image of FIG. 3b. When cross-sectional planes are taken through the 3D image of the aortic root, the true size and shape of the lumens at the landmark points can be fully observed and measured.

Figure 4:
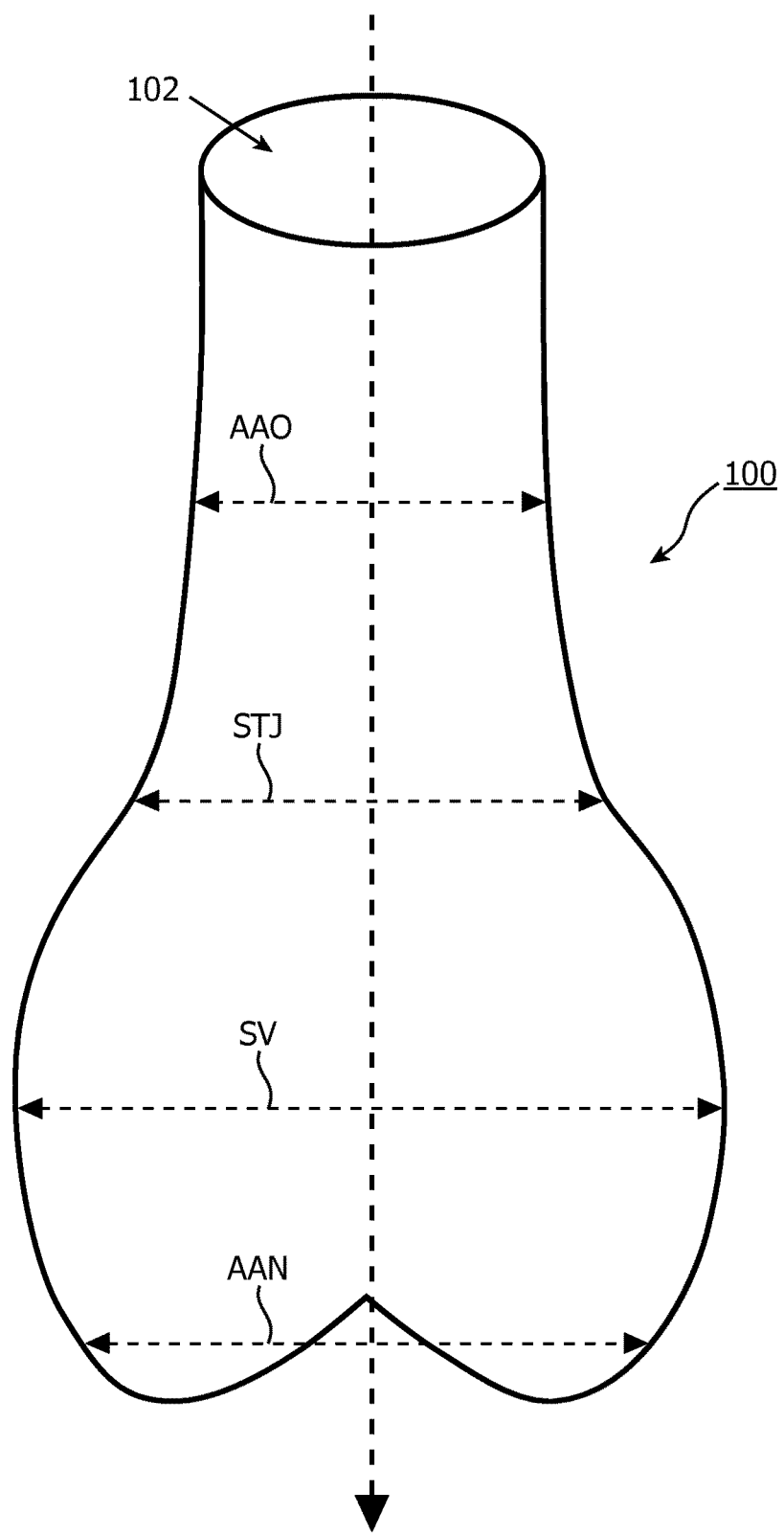
FIG. 4 illustrates a heart model of an aortic root and a portion of the ascending aorta.
Figure 6A:
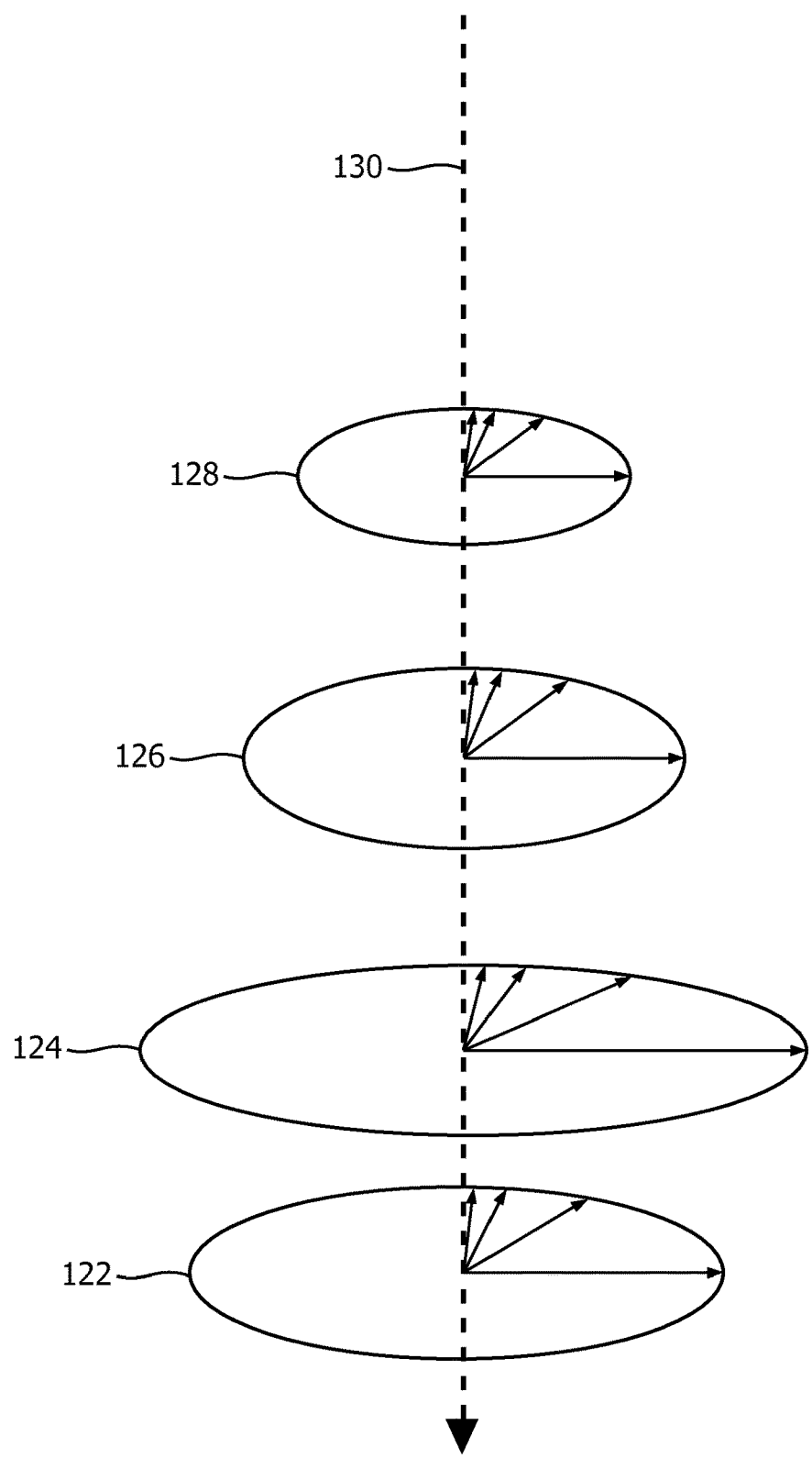
FIG. 6a illustrates the aortic root model of FIG. 4 in which cross-sections of the model are initially represented as ellipses.

FIG. 4 illustrates an aortic root model 100 in a longitudinal view along the medial axis and constructed in accordance with the present invention. The shape of the model 100 in this view is seen to be an idealized shape of the endothelial lining of the aortic root. The model is of the interior of the lumen, as that is the volume into which an implant must properly fit. In this view the model is annotated by the same landmark regions shown in FIGS. 3a and 3b, the aortic annulus (AAN), the sinuses of Valsalva SV, sinotubular junction STJ, and the ascending aorta (AAo) near the top. This model 100 exhibits the starting shape before fitting the model to the aortic root anatomy of a patient in a 3D ultrasound image. In the third dimension of this 3D model, the cross-sectional areas 102 start as ellipses as shown in FIG. 6a but can be extended to other shapes and irregular planar contours as discussed more fully below.

Figure 5A:
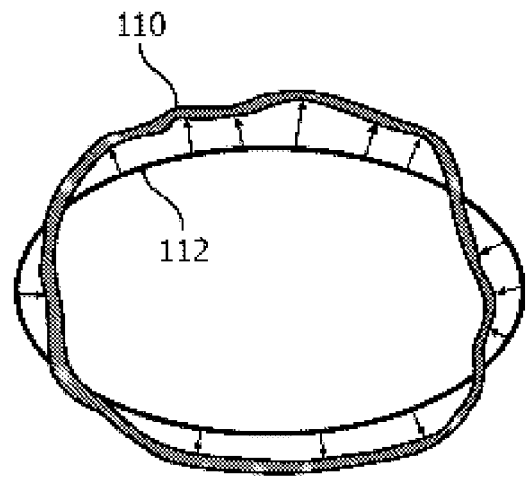
FIG. 5a illustrates an automated technique for fitting an aortic root heart model to the size and shape of the aortic root of a three dimensional ultrasound image.
Figure 5B:
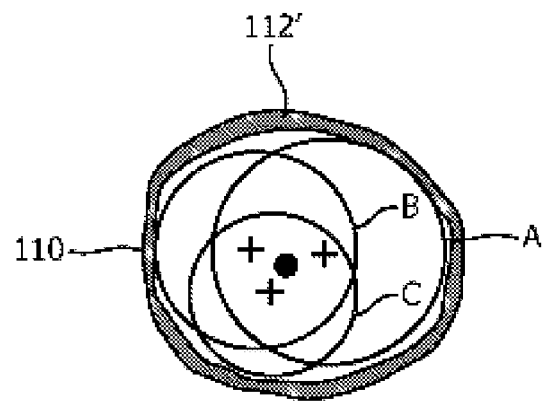
FIG. 5b illustrates an automated technique for locating the medial axis of an adjusted model of the aortic root.

Various techniques are knows for fitting a contour model such as aortic root model 100 to boundaries in an anatomical images. See the Weese et al. patent referenced above. See also International Patent Appl. No. IB2010/052756 (Peters et al.), filed Jun. 18, 2010 and entitled "Establishing A Contour of A Structure Based On Image Information." Techniques for fitting the model 100 to the endothelial lining of the aortic root in an ultrasound image and locating the medial axis in an adjusted and registered model are illustrated in FIGS. 5a and 5b. FIG. 5a illustrates a cross-sectional slice view of the endothelial lining 110 of the aortic root taken through the 3D ultrasound image, which may be formed by MPR reconstruction of the 3D dataset along a selected plane. As mentioned above, the cross-sections of the model 100 can be circular, elliptical, irregular, or other closed contour shapes. An elliptical cross-section 112 of the model 100 at the level of the MPR view is shown in FIG. 5a. The elliptical cross-section 112 is adjusted by moving the ellipse in directions orthogonal to the ellipse surface in search of the endothelial lining, which can be recognized by the gradient in the image data at the boundary. In the example of FIG. 5a, the endothelial boundary is outside of the elliptical cross-section at the top and bottom of the ellipse, and so an outward search for the gradient from the elliptical cross-section 112 in these regions will move these regions of the ellipse outward to match the endothelial lining 110. At the left and right sides, the elliptical cross-section is seen to be outside of the endothelial lining 110, and so an inward search from the starting position of the elliptical cross-section 112 in these regions will locate the boundary gradient in the image data at locations inward from the starting position of the ellipse. The small arrows in FIG. 5a indicate the orthogonal directions in which the search for the gradient will find the walls of the aortic root starting from the initial elliptical shape of the model.

With the ellipses or other closed contour shapes at the different levels of the model aligned with the shape of the aortic root as seen in the 3D image data, the medial axis of the adjusted model can be located as indicated in FIG. 5b. This drawing illustrates a method of polygon-fitting to find the central axis of the adjusted model. This is a mathematical process in which circles or polygons are located inside the aortic root shape including the endothelial lining 110 or preferably the co-aligned cross section of the model. Each circle A, B, and C in the example of FIG. 5b is located tangential to the endothelial lining or the adjusted model and has a diameter which is the largest to enable the circle/polygon to remain entirely within the lumen. A plurality of such circles/polygons are located around the interior boundary of the anatomy including the endothelial lining 110 or adjusted model 112'. In this drawing the circles A, B, and C are of different (smaller) sizes than would be used for clarity of illustration. Each circle/polygon located in the lumen in this manner has its own center as indicated by the "+" symbols.

When the locations of the "+" symbols are averaged, they yield a nominal center as indicated by the small solid circle in the drawing. The location of the nominal center shown by the small solid circle is taken as the location of the medial axis in the plane of this cross-section, and a sequence of such nominal centers determined for a plurality of different cross-sectional levels through the aortic root or model 100 will indicate the path of the medial axis through the adjusted model.

Figure 6B:
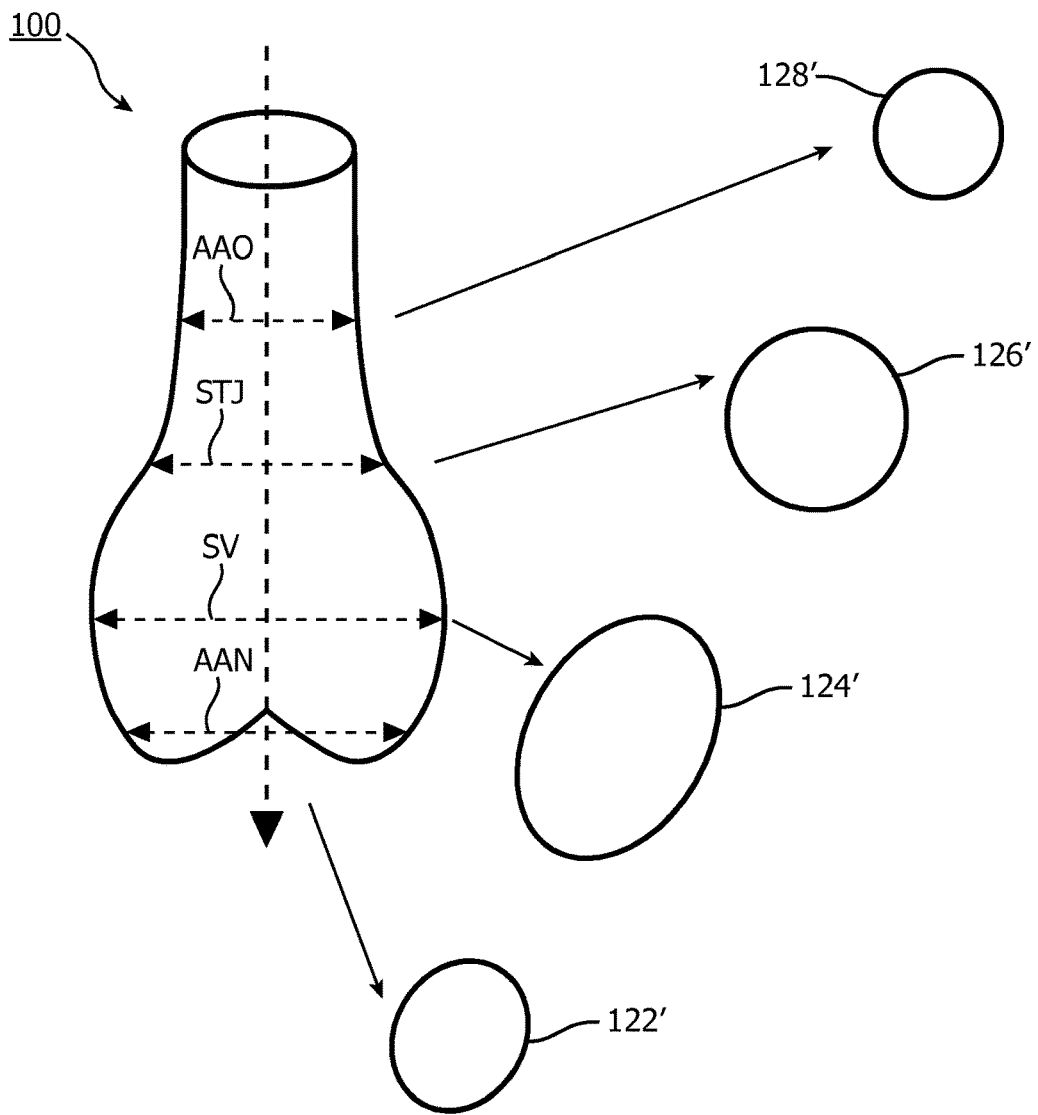
FIG. 6b illustrates an aortic root model in which the cross-sections are of various closed contour shapes.

FIG. 6a illustrates four of the elliptical cross-sections 122, 124, 126, and 128 of the aortic root model 100 for the four landmark levels noted in FIG. 4, as located along the medial axis 130 of the model. As previously mentioned, other closed contour shapes and even irregular shapes can serve as the shapes of the cross-sectional areas of the aortic root model. The model 100 in FIG. 6b, for example, uses a small ellipse 122' and a larger ellipse 124' with a longer major diameter as the cross-sectional shapes for the AAN and the SV, respectively. At the STJ and the AAO landmarks circles 126' and 128' are used as the cross-sectional shapes. Other closed contours may also be used. In the model with elliptical cross-sections shown in FIG. 6a, each ellipse has a particular radius value as a function of the radial direction outward from the medial axis as shown by the arrows on each ellipse. After the ellipses are adjusted to fit the anatomy of the aortic root, each radius indicates the distance to the aortic root in its radial direction. These radii can be measured, counted, and the results displayed in a histogram 140 as shown in FIG. 7. The histogram 140 is divided into four bins, each for the radii of a different ellipse. The first bin 142 is of the radii of ellipse 128, and so on. For the perfectly elliptical model 100 prior to registration with the anatomy, the distribution of the number of radii in the bins will produce a histogram as shown in FIG. 7. The peak of each segment of the histogram shows the maximum radius of the ellipse, which is in line with its longest diameter. Each successive peak of the histogram 140 is seen to be at a level corresponding to the size of the ellipse at that level. The same histogram can be produced from the model 100 after each ellipse has been adjusted to be aligned with the anatomical boundary of the aortic root. The histogram 140 will then show the peaks and distributions of radii at the four landmark locations of the aortic root, and is data that can be used to produce a prosthetic aortic valve that is custom sized for the particular patient.

Figure 9:
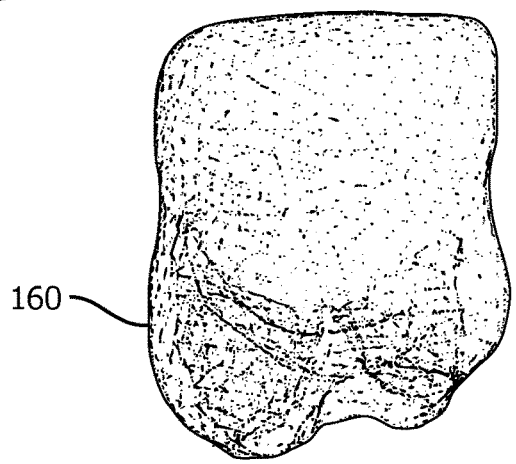
FIG. 9 illustrates an aortic root mesh model constructed in accordance with the principles of the present invention.

This process can be repeated beyond the four land mark levels shown in FIG. 4. The fitting of the model 100 to the anatomy shown in the 3D ultrasound image can be repeated for other closed contour cross-sections at closely spaced levels along the medial axis, producing the measurements of closely spaced adjusted closed contours along the medial axis. In FIG. 8, each line 150 represents the radial measurements of adjusted closed contours for the four landmark levels 122', 124', 126' and 128', shown as individual lines in this drawing, interspersed with the values from other adjusted closed contours at intermediate levels along the medial axis. While FIG. 8 illustrates the adjusted shapes at seventeen levels of the aortic root, the process can be repeated for hundreds of closely spaced levels. When the tips of the radial arrows in their respective radial directions are joined, they define the surface of the interior boundary of the aortic root and thus form a three dimensional mesh model 160 of the interior walls of the aortic root as illustrated in FIG. 9, which also illustrates the aortic valve leaflets. This three dimensional mesh model and its measurements, including tags marking the location of the coronary artery ostia, can be provided at an output 56 of the ultrasound system in the form of a printout or an electronic data file for a manufacturer of prosthetic aortic valves for the fabrication of a custom-designed valve replacement that is precisely sized for a particular patient.

Since a matrix array probe can produce 3D images of the aortic root region at a frame rate that produces many 3D images over the span of a heart cycle, 3D images at many different phases of the heart cycle are available for model fitting. The above procedure can be repeated to fit the aortic root model to the 3D ultrasound image at each imaged phase of the heart cycle, thereby producing a sequence of model images which model the lumen size and shape and coronary ostia location at each phase of the heart's motion. This sequence of fitted models can be provided to the prosthetic valve designer to assure that the prosthetic valve fits and operates properly over the entire cycle of the heart's motion. The 3D model images can be replayed in phase sequence in a 3D kinetic parallax presentation, enabling the designer to observe and assess the motion and changing shape of the lumen and ostia during the heart cycle, and used to assure that a precisely fitting prosthetic valve is produced.

What is claimed is:

1. An ultrasound system which is used to plan a surgical procedure with an implantable device in an aortic root, comprising:
   an ultrasound probe adapted to scan a volumetric region including an aortic root;
   an image generator coupled to the ultrasound probe and configured to produce a three dimensional ultrasonic image of the aortic root;
   electronic circuitry comprising a 3D shape processor that is configured to:
      receive the three dimensional ultrasonic image of the aortic root and a three dimensional anatomical model of the aortic root, electronically stored in memory on the ultrasound system;
      fit closed contour cross-sections of the anatomical model to a shape of the aortic root in the three dimensional ultrasonic image to adjust a shape of the anatomical model to fit the aortic root in the three dimensional image;
      produce a scaled model of the aortic root;
      locate a medial axis of the scaled model by determining a center point of each closed contour cross-section of the scaled model, wherein the determining the center point comprises locating a plurality of circles or polygons around an interior of the closed contour cross-section and averaging the centers of the plurality of circles or polygons to yield the center point of each closed contour cross-section;
      produce measurements of the closed contour cross-sections at a plurality of locations along the medial axis of the scaled model of the aortic root;
      produce a histogram of the measurements; and
      determine at least one peak of the histogram;
   a display coupled to the image generator and the 3D shape processor and configured to display the three dimensional ultrasonic image of the aortic root; and
   an output at which data corresponding to the measurements of closed contour cross-sections at the plurality of locations along the medial axis of the scaled model of the aortic root and the at least one peak is provided to produce a custom implantable device.

2. The ultrasound system of claim 1, wherein the closed contour cross-sections of the scaled model are produced for key anatomical landmarks of the aortic root.

3. The ultrasound system of claim 2, wherein the three dimensional anatomical model exhibits a plurality of elliptical cross-sections along the medial axis at locations corresponding to anatomical landmarks of an aortic root.

4. The ultrasound system of claim 3, wherein the elliptical cross-sections corresponding to anatomical landmarks of the aortic root are fitted to an endothelial lining in the three dimensional ultrasonic image of the aortic root.

5. The ultrasound system of claim 4, wherein the elliptical cross-sections are fitted to the endothelial lining by recognizing a gradient in the three dimensional ultrasonic image.

6. The ultrasound system of claim 1, wherein the closed contour cross-sections of the scaled model are circles or ellipses or both, and the measurements are radial measurements.

7. The ultrasound system of claim 1, wherein the 3D shape processor is further configured to make radial measurements from the medial axis to a border of the anatomical model.

8. The ultrasound system of claim 7, wherein the 3D shape processor is further configured to identify a three dimensional surface of the anatomical model from the radial measurements.

9. The ultrasound system of claim 8, wherein the three dimensional surface further comprises a mesh model of the aortic root of the three dimensional ultrasonic image.

10. The ultrasound system of claim 9, wherein the mesh model is provided at the output to produce the custom implantable device.

11. The ultrasound system of claim 1, wherein the three dimensional anatomical model is stored and the 3D shape processor is located on a workstation separate from the ultrasound probe and image generator.

12. The ultrasound system of claim 1, wherein the custom implantable device is a prosthetic aortic valve replacement.

13. The ultrasound system of claim 1, wherein the measurements of the closed contour cross-sections at a plurality of locations along the medial axis of the scaled model of the aortic root are found for different phases of a heart cycle.

14. The ultrasound system of claim 1, wherein the display is further configured to display the histogram.

15. The ultrasound system of claim 1, wherein the at least one peak of the histogram corresponds to a measurement at a location of a key anatomical landmark.

* * * * *